United States Patent
Verkaart

[19]
[11] Patent Number: 6,071,095
[45] Date of Patent: Jun. 6, 2000

[54] CONTAINER WITH INTEGRAL PUMP PLATEN

[75] Inventor: Wesley H. Verkaart, Norwell, Mass.

[73] Assignee: Harvest Technologies Corporation, Norwell, Mass.

[21] Appl. No.: 09/051,482

[22] PCT Filed: Oct. 18, 1996

[86] PCT No.: PCT/US96/16770

§ 371 Date: Jun. 17, 1998

§ 102(e) Date: Jun. 17, 1998

[87] PCT Pub. No.: WO97/14450

PCT Pub. Date: Apr. 24, 1997

Related U.S. Application Data

[60] Provisional application No. 60/008,127, Oct. 20, 1995, provisional application No. 60/008,128, Oct. 20, 1995, and provisional application No. 60/005,772, Oct. 20, 1995.

[51] Int. Cl.[7] .................................................. F04B 43/08
[52] U.S. Cl. .................................. 417/477.9; 210/416.1; 210/436; 210/512.1; 422/122; 604/319; 604/406
[58] Field of Search ............... 417/477.9; 422/102; 604/319, 406; 210/416.1, 436, 512.1

[56] References Cited

U.S. PATENT DOCUMENTS

| | | | |
|---|---|---|---|
| 4,135,647 | 1/1979 | Mascia et al. | 222/211 |
| 4,275,731 | 6/1981 | Nichols | 128/276 |
| 4,681,571 | 7/1987 | Nehring | 604/320 |
| 5,000,351 | 3/1991 | Rudick | 222/105 |
| 5,087,250 | 2/1992 | Lichte et al. | 604/321 |
| 5,330,431 | 7/1994 | Herskowitz | 604/153 |
| 5,372,709 | 12/1994 | Hood | 210/90 |
| 5,429,486 | 7/1995 | Schock et al. | 417/477.9 |
| 5,458,567 | 10/1995 | Cathcart | 604/4 |
| 5,512,042 | 4/1996 | Montoya et al. | 604/4 |

FOREIGN PATENT DOCUMENTS 0254607  1/1988  European Pat. Off. .

*Primary Examiner*—Ronald Capossela
*Attorney, Agent, or Firm*—Clark & Brody

[57] ABSTRACT

A container (400) for the collection of fluids in a vacuum system includes upper and lower chambers (402, 404). Fluids are admitted to the upper chamber (402) to form a vortex and separate fluid and debris from air. The fluids then pass to the lower chamber (404) through a filter (412). A discharge tube (428) is connected to the lower chamber (404) to allow the accumulated fluids to be pumped from the container (400). The bottom of the lower chamber (404) includes a recess (430) that forms a platen for a roller pump, and a discharge tube (428) is located adjacent the platen whereby rollers (426) engage the tube (428) and platen upon installation of the chamber (400) on a base. A second port (418) is provided to the upper chamber (402) for admission of a second fluid such as an anticoagulant.

17 Claims, 1 Drawing Sheet

CONTAINER WITH INTEGRAL PUMP PLATEN

CROSS REFERENCE TO RELATED APPLICATIONS

This application claims benefit of U.S Provisional Pat. Application Nos. 60/008,127, 60/008,128; and 60/005,772 all filed Oct. 20, 1995.

TECHNICAL FIELD

This invention relates to the art of articles for the collection and discharge of fluids. In particular, the invention relates to a disposable container for the collection of physiological fluids and transfer of the fluids to another container.

BACKGROUND

It is known to collect fluids, such as blood, from surgical sites with the use of vacuum pressures. The blood thus collected is often treated to remove air and particulate contaminates. Known filters for physiological fluids typically employ such features as a tubular inlet directed tangential to a cylindrical inlet chamber to generate centrifugal forces for separating the air from collected liquid and physical filters for further removal of particulate contaminates. These devices, however, do not lend themselves to easy discharge of the collected fluids and do not provide for effective treatment of the collected blood with anticoagulants, and the like.

SUMMARY OF THE INVENTION

In accordance with the invention, a blood collection chamber includes a vacuum chamber for accumulating a collected fluid, such as blood or other physiological fluids. An integral portion of the container forms at least a portion of a pump for discharging the collected fluid from the container. In the preferred embodiment, the chamber is used in a system for vacuum collection of blood and other physiological products from a surgical site.

The container is divided into upper and lower chambers. The upper chamber is cylindrical and receives the fluid from the surgical site and performs an initial separation of air and debris from the fluid. The initial separation is accomplished by directing the fluid into the chamber to form a vortex. The fluid is then passed through a filter between the upper and lower chambers for further cleaning. In the preferred embodiment, the vortex is created by introducing the fluids in a direction tangent to the upper chamber. A vacuum port communicates with the lower chamber to create a pressure differential that draws fluids from the surgical site into the upper chamber and then from the upper chamber into the lower chamber with the assistance of gravity.

The upper chamber is provided with a port for admitting a second fluid to be mixed with the collected fluids. In the preferred embodiment, the second fluid is an anticoagulant. The amount of anticoagulant drawn into the chamber is a function of the level of the vacuum pressure. Accordingly, more anticoagulant is drawn in as more fluid is drawn in, which tends to maintaining the proportion of the anticoagulant to that of the fluid collected in the container. This obviates the need for a separate pump or metering device for the anticoagulant.

An additional feature of the invention is the means by which the collected fluids are discharged from the container. Because the container is under negative pressure, the collected fluids must be pumped out of the container. A known type of pump is a roller pump, and the bottom of the lower chamber is formed into a platen for such a roller pump. The outlet tube is positioned adjacent the platen such that it will be pushed against the platen by the rollers when the chamber is placed onto the roller. Thus, the roller pump will be automatically loaded with the tubing and will be capable of operation immediately after the chamber is placed on the support containing the roller.

DETAILED DESCRIPTION OF THE PREFERRED EMBODIMENT

Figure 1:
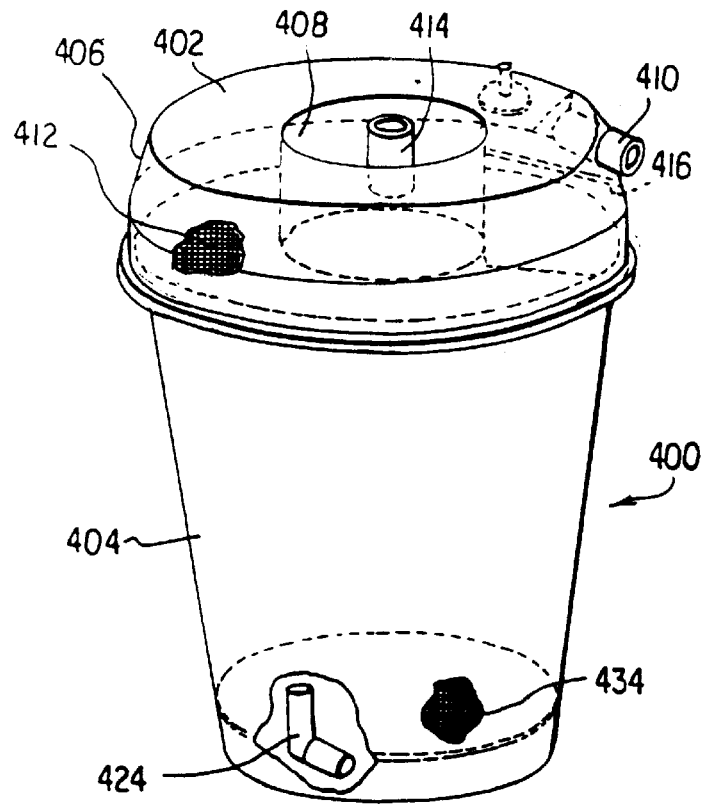
FIG. 1 is a perspective view of a chamber in accordance with the invention.
Figure 2:
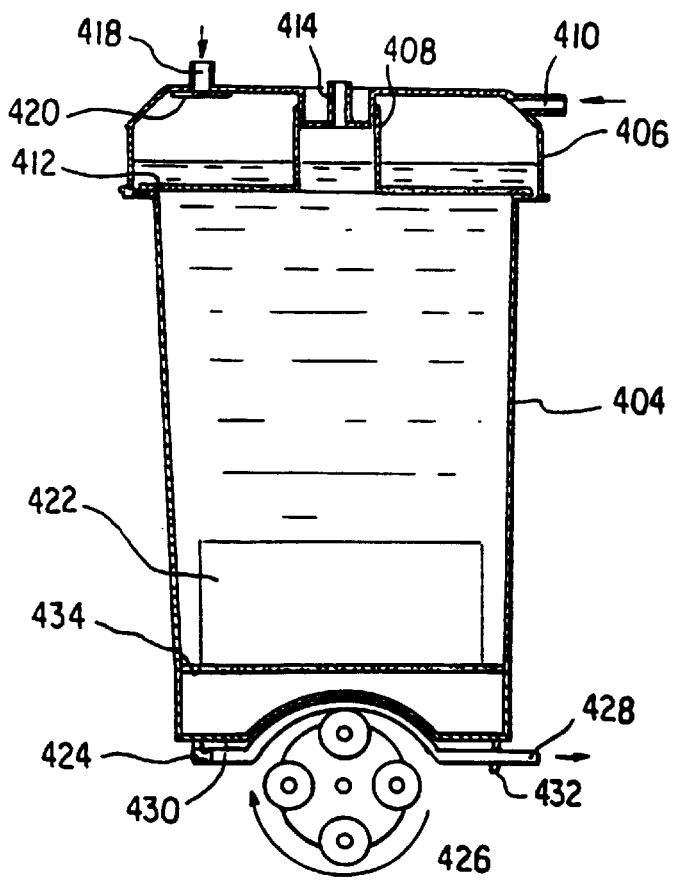
FIG. 2 is a transverse cross section of the chamber shown in FIG. 1 and installed on a roller pump base.

With reference to FIG. 1, a chamber 400 in accordance with the invention comprises an upper element 402 that is attached to a lower element 404. The upper element includes an outer wall 406 and an inner wall 408, which form a generally cylindrical upper chamber, and a fluid inlet 410. The floor of the upper chamber includes a particulate filter 412 having openings in the range of $400\mu$ to $600\mu$. A vacuum port 414 communicates with an inner cavity formed by the wall 408, and this cavity is in open communication with the lower chamber formed by the lower element 404.

When vacuum, for example as obtained from a vacuum pump (not shown) is applied to the port 414, air and fluid are drawn into the inlet 410. The inlet is preferably tubular, and the axis of the tube is tangential to the upper chamber. The incoming fluid from the surgical site thus forms a vortex in the upper chamber to begin the separation of air and debris from the liquid. The vortex is terminated by a baffle 416, and the fluid and air are then caused to pass through the filter 412 removing debris from the fluid. The fluid and air pass through filter 412 both by the forces of gravity and by the pressure gradient existing between the upper and lower chambers created by the presence of the filter 412.

A second fluid, preferably an anticoagulant, is introduced to the fluid in the upper chamber through port 418. For example, a bag of anticoagulant may be hung above the container and connected to the port 418 by a flexible tube. The bottom of the port 418 is covered by a porous disk 420, which in turn communicates with the upper chamber. The amount of anticoagulant drawn into the upper chamber will depend in large measure on the level of the vacuum in the upper chamber. Thus, as the vacuum increases, more fluid is drawn through inlet 410, and more anticoagulant is drawn in through port 418. This causes the proportion of anticoagulant in the mixture of collected fluid and anticoagulant to remain constant when the vacuum levels are controlled. Moreover, because the disk presents a relatively large surface area to the upper chamber, the pressure in the port 418 is easily made large enough to draw the desired amount of anticoagulant into the fluid without the use of another mechanical pump for the desired levels of vacuum in the inlet port 410.

In the preferred embodiment, the vacuum pressure applied to the port 414, is controlled whereby the vacuum pressure is increased (e.g., to about −100 mm Hg) only in response to detection of fluids in the collection tube that communicates with the port 410. When the system determines that no fluid is present in the collection tube, as by sensing the pressure drop across a restriction in the collection line, the vacuum pressure is reduced to a much smaller level (e.g., about −20 mm Hg). Thus, when the system is not collecting fluid, little or no anticoagulant is drawn into the chamber due to the reduced-vacuum.

The disk 420 is preferably made of a known porous material, such as sintered polyethylene, with pores in the range of from 10 $\mu$ to 20$\mu$. Alternatively, a mechanical valve may be used separately or in conjunction with the porous disk. The ease of passage of the anticoagulant will depend on such variables as the hydrophobicity of the material, the thickness, and the geometry of the disk, or in the case of the valve, cracking pressure or restriction to flow.

The fluid 422 collected in the chamber will accumulate in the lower chamber. The chamber, however, further includes means for discharging the fluid 422 through a discharge port 424. The discharge means preferably comprises a roller pump, and the pump includes a roller assembly 426 of known construction mounted for rotation about a horizontal axis. A roller pump requires a platen for cooperation with the roller assembly, and this platen in formed into the bottom of the chamber in accordance with the invention. Thus, a flexible outlet line 428 is connected to the discharge port 424 adjacent a recess 430 in the bottom of the chamber, which forms a platen for the roller pump. The outlet line 428 is supported just below the platen 430 by engagement with the port 424 and a clip 432. When the chamber is placed on the roller 426, the line 428 is pushed upward to engage the platen 430 and be compressed between the platen and the rollers. The collected fluids are then discharged by rotation of the roller 426.

If desired, a second filter 434 may be placed above the discharge port to provide additional cleaning of the fluids prior to discharge.

Modifications within the scope of the appended claims will be apparent to those of skill in the art.

I claim:

1. Apparatus for collection of fluids comprising a chamber formed by an upper element and a lower element, wherein said upper element comprises an upper chamber formed between an outer wall and an inner wall and said inner wall forms an inner cavity in communication with said lower element, a vacuum port connected to said inner cavity for conducting air from said chamber and reducing the pressure in said chamber, a fluid inlet for admitting a first fluid into said upper chamber in response to reduced pressure in said chamber, and means for discharging said fluids from said chamber.

2. Apparatus according to claim 1 further comprising a second port for admitting a second fluid to said upper chamber in response to said reduced pressure for mixing with said first fluid in said upper chamber, means attached to said second port for controlling the flow of said second fluid into said upper chamber such that the amount of said second fluid drawn into said chamber is in approximately fixed proportion to the amount of said first fluid drawn into said chamber.

3. Apparatus according to claim 2 wherein said means attached to said second port is a porous disk.

4. Apparatus according to claim 1 wherein said upper chamber receives said first fluid from the exterior of said chamber and forms therein a vortex flow in said first fluid.

5. Apparatus according to claim 4 wherein said means for discharging comprises a discharge port connected to said lower element.

6. Apparatus according to claim 5 wherein said means for discharging further comprises a flexible outlet line connected to said discharge port and a roller-pump platen formed in said lower element adjacent said flexible outlet line.

7. Apparatus according to claim 6 wherein said platen is formed in a bottom surface of said lower element.

8. Apparatus according to claim 1 wherein said fluid inlet is positioned with respect to said upper element to form a vortex flow in said first fluid.

9. Apparatus for collection and discharge of fluids comprising a chamber for receiving said fluids, a fluid inlet for admitting said fluids to said chamber, a discharge port for allowing said fluids to flow out of said chamber, a flexible outlet line attached to said discharge port for carrying discharged fluids, and a recess in said chamber adjacent said flexible outlet line, said recess forming a platen for engaging said flexible outlet line when said flexible outlet line is pushed into engagement with said recess by rollers to pump said fluids through said discharge port.

10. Apparatus according to claim 9 wherein said recess is in the bottom of said chamber.

11. Apparatus according to claim 9 wherein said chamber comprises an upper element and a lower element in fluid communication with said upper element and said fluid inlet is tangentially located in said upper element to form a vortex flow in said fluids that are admitted to said upper element.

12. Apparatus according to claim 11 wherein said upper element is cylindrical.

13. Apparatus according to claim 11 further comprising a vacuum port in communication with said lower element.

14. Apparatus according to claim 13 wherein said vacuum port communicates with an inner cavity formed in said upper element, said inner cavity being in communication with said lower element.

15. Apparatus according to claim 13 further comprising a clip for supporting one end of said flexible outlet line.

16. Apparatus according to claim 13 further comprising a filter between said upper and lower elements for removing particulates from said fluids passing from said upper element to said lower element.

17. Apparatus according to claim 9 wherein said chamber comprises an upper element and a lower element, said upper chamber is formed between an outer wall and an inner wall, and said inner wall forms an inner cavity in communication with said lower element, and further comprising a vacuum port connected to said inner cavity for conducting air from said chamber and reducing the pressure in said chamber.

\* \* \* \* \*